(12) United States Patent
Nichols et al.

(10) Patent No.: US 6,266,566 B1
(45) Date of Patent: Jul. 24, 2001

(54) WAVEFORM NORMALIZATION IN A MEDICAL DEVICE

(75) Inventors: Timothy J. Nichols, Lino Lakes; Paul Blowers, St. Paul; A. Martin Bradley, Plymouth; Robert Werner, Minnetonka, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/316,589

(22) Filed: May 21, 1999

(51) Int. Cl.[7] ............................................. A61N 1/37
(52) U.S. Cl. ..................................... 607/30; 607/59
(58) Field of Search .................... 607/30, 32, 59, 607/60; 600/525, 523

(56) References Cited

U.S. PATENT DOCUMENTS 5,345,362   9/1994   Winkler .
5,402,794   4/1995   Wahlstrand et al. .
5,578,063 * 11/1996  Bocek et al. ............................ 607/5
5,716,384   2/1998   Snell .
5,724,985   3/1998   Snell et al. .
5,782,890   7/1998   Wahlstrand et al. .
5,833,623  11/1998   Mann et al. .

* cited by examiner

Primary Examiner—George R. Evanisko
(74) Attorney, Agent, or Firm—Beth L. McMahon

(57) ABSTRACT

An apparatus and method for normalizing waveform information displayed on a medical device. This waveform normalization allows the user to quickly adjust individual waveforms if they exceed the normal viewing range on the display. An electrogram signal is received from an implantable medical device. The electrogram signal is continuously transformed into a plurality of voltage data samples. A waveform is created from the plurality of voltage data samples, and the waveform is displayed on a medical display device. A user selectable waveform normalization control is located adjacent each displayed waveform on the medical display device. Upon activation of the waveform normalization control, the adjacent waveform is normalized to a pre-determined nominal height on the display.

41 Claims, 11 Drawing Sheets

WAVEFORM NORMALIZATION IN A MEDICAL DEVICE

THE FIELD OF THE INVENTION

The present invention generally relates to data normalization, and more particularly to user selectable normalization of individual waveforms displayed on a medical device.

BACKGROUND OF THE INVENTION

Programmers are used to initialize and service various implanted devices for cardiac therapy. These devices include pacemakers, cardioversion/defibrillator devices, and so on. Presently, typical programmers provided to the physician are generally the size and shape of a portable or laptop computer. Communication with an implanted device is accomplished through inductive coupling by using an accessory connected to the programmer, commonly called a "wand". The programmers further include a screen for displaying alphanumeric information, and, optionally, to display graphic information such as an electrogram (EGM) or an electrocardiogram (ECG). The programmer may also include a printer for printing information, such as the programming parameters set for a particular pacemaker, data logged by the pacemaker for a pre-selected period, or an ECG.

Programmers may also contain an analyzer which is used to assess pacing lead performance during a pacemaker or defibrillator implantation or during lead system troubleshooting. By measuring a lead's electrical performance, the analyzer aids the implanting physician in selecting an electrically appropriate site for the placement of the implanted device.

Pacing leads are insulated wires that carry precisely controlled electrical impulses from a pacemaker implanted in the upper chest to the inner wall of the heart. The analyzer utilizes software to provide an implanting physician with a dynamic display of key pacing and sensing measurements, and a display of waveform which enable the physician to rapidly select an appropriate site for lead placement.

When viewing waveform information on the programmer/analyzer display, variations in the signal gain of the displayed waveform can cause wide variations in the height of the displayed waveform, creating legibility problems. Signal gain variations are typically encountered when the device operator switches display modes (e.g., switching between pacing and sensing modes). In such a mode switch, the polarization following pacing pulses is large and can infringe on other waveforms on the display.

Controls are typically provided on the programmer/analyzer for incrementally adjusting the height of the waveform on the display. However, such controls require frequent adjustments, and it often takes an unacceptably long period of time to adjust the waveform to an optimal size, resulting in the potential loss of critical display data.

Another approach to the problem of waveforms exhibiting different amplitude characteristics is the use of a "normalize all waveforms" control on the programmer. While the "normalize all waveforms" control provides a quick method of normalizing all waveforms on a programmer/analyzer display to a predefined height, this "all or nothing" approach to waveform normalization is not acceptable for applications where individual leads (e.g., EGM and ECG) may be attached, repositioned, or unattached during a lead test.

Other disclosures relating to the same general problem include the U.S. Patents listed below in Table 1.

TABLE 1

Prior Art Patents

| Patent No. | Title |
|---|---|
| 5,033,623 | System and Method for Facilitating Rapid Retrieval and Evaluation of Diagnostic Data Stored by an Implantable Medical Device |
| 5,402,794 | Method and Apparatus for Heart Transplant Monitoring and Analog Telemetry Calibration |
| 5,716,384 | Method and System for Organizing, Viewing and Manipulating Information in Implantable Device Programmer |
| 5,724,985 | User Interface for an Implantable Medical Device Using an Integrated Digitizer Display Screen |
| 5,782,890 | Method for Heart Transplant Monitoring and Analog Telemetry Calibration |

At least some of the devices and methods disclosed in the patents of Table 1 may be modified advantageously in accordance with the teachings of the present invention.

SUMMARY OF THE INVENTION

The present invention overcomes the disadvantages of the prior art by providing an apparatus and method for automatically adjusting the display height of an individually selectable cardiac waveform to a predetermined nominal size on a programmer/analyzer display.

The present invention has certain objects. That is, the present invention provides solutions to certain problems existing in the prior art such as the display of waveform data from implantable medical devices wherein: (a) the height of displayed waveforms is difficult to control due to changes in the signal gain upon mode change operations; (b) adjusting the height of an individual waveform with existing incremental sizing controls is cumbersome and time consuming; and (c) concurrently adjusting the height of all waveforms in a display through a single normalization operation becomes impracticable when individual leads (e.g., EGM and ECG) corresponding to a single waveform may be attached, repositioned, or unattached during a lead test.

At least some embodiments of the present invention include one or more of the following advantages: (a) increased flexibility in that each waveform is independently adjustable through its own corresponding normalization function; (b) operational simplicity and efficiency in that a user need only activate one button to normalize an individual waveform, and the normalize button is positioned adjacent its corresponding waveform; and (c) expanded usability in that the normalization function is available in a number of different display modes, including: a waveform adjust screen, a lead analysis screen, a threshold test screen, and an advanced test mode screen.

The present invention has certain features, including a programmer/analyzer including a user interface consisting of a display and means for displaying several graphic elements. The graphic elements include at least one waveform element showing a time dependent parameter related to a cardiac function, such as an ECG or EGM. The programmer/analyzer further includes a user selectable waveform normalization graphic element associated with each displayed waveform element which, upon activation, adjusts the waveform to a predetermined nominal size on the display. In a display having two or more adjacent waveforms, each user selectable waveform normalization graphic element operates only on its associated waveform.

The user selectable waveform normalization graphic element is available within several display modes of the programmer/analyzer, including: a live waveform adjust screen, a lead analysis screen, a threshold test screen, and an advanced test screen.

Other features, advantages, and objects of the invention will become apparent by referring to the appended drawings, detailed description, and claims.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
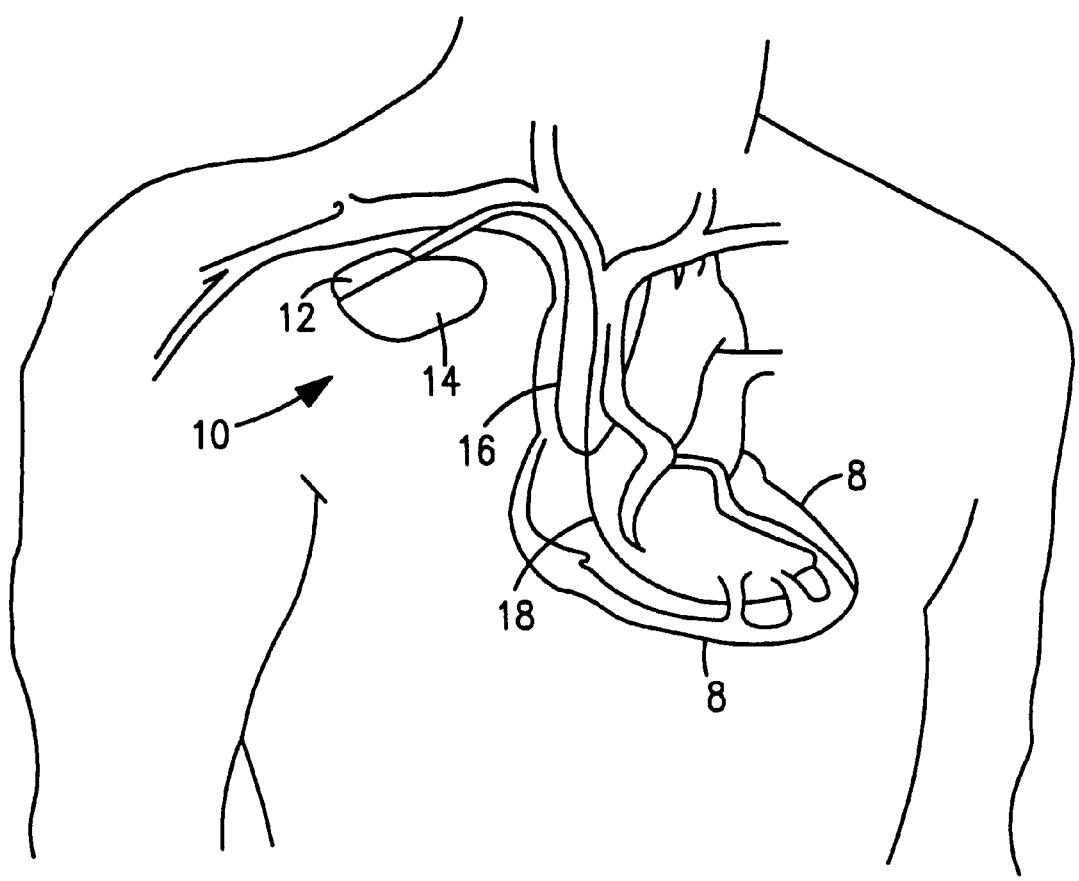
FIG. 1 is a simplified schematic view of one embodiment of an implantable medical device (IMD) used in conjunction with the present invention.

FIG. 1 is a simplified schematic view of one embodiment of implantable medical device ("IMD") 10 used in conjunction with the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
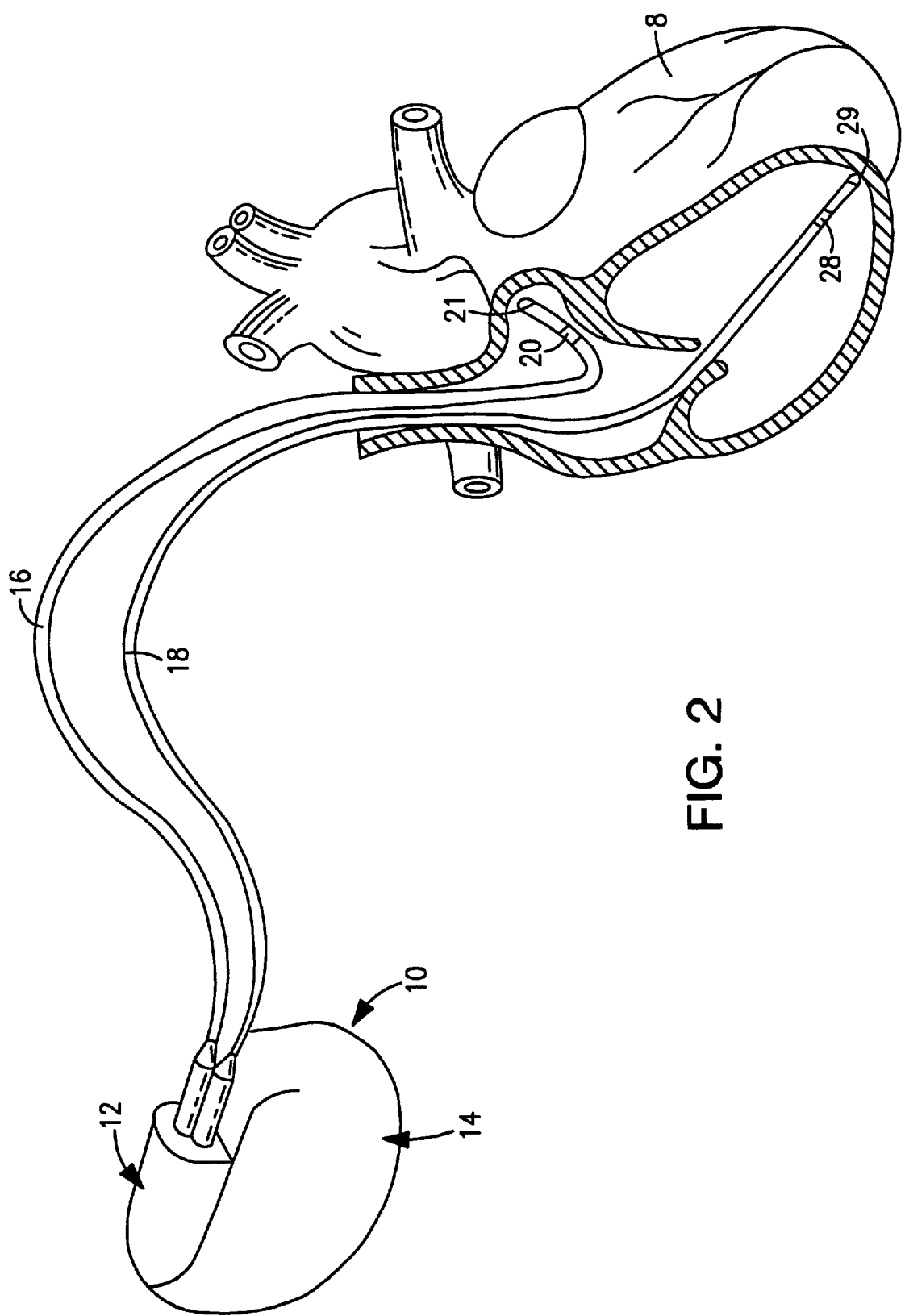
FIG. 2 is an illustration of the implantable medical device (IMD) and associated leads from FIG. 1.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
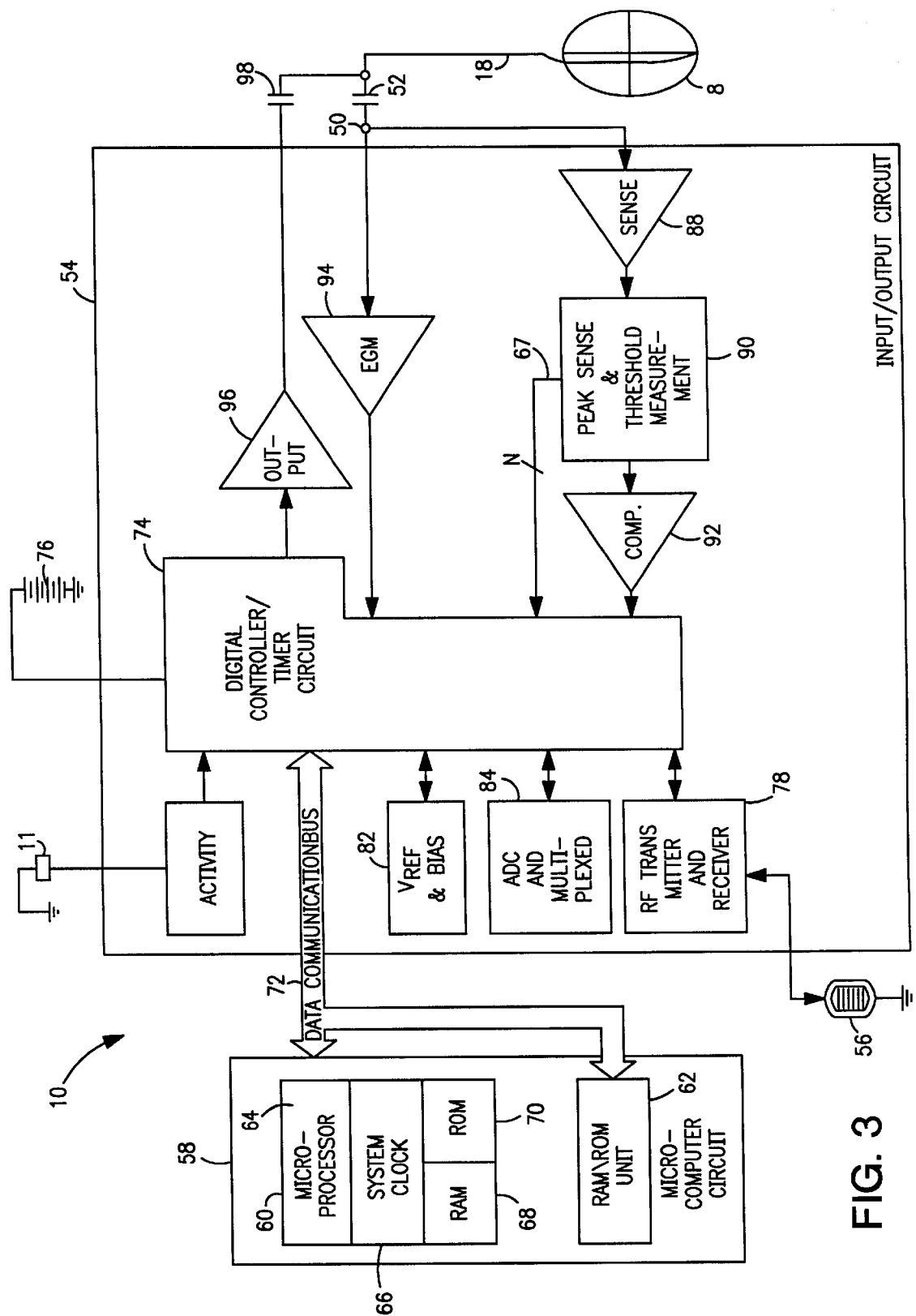
FIG. 3 is a block diagram showing a portion of the circuitry of the implantable medical device (IMD) of FIG. 1 and an external programmer.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hennetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wybomy et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
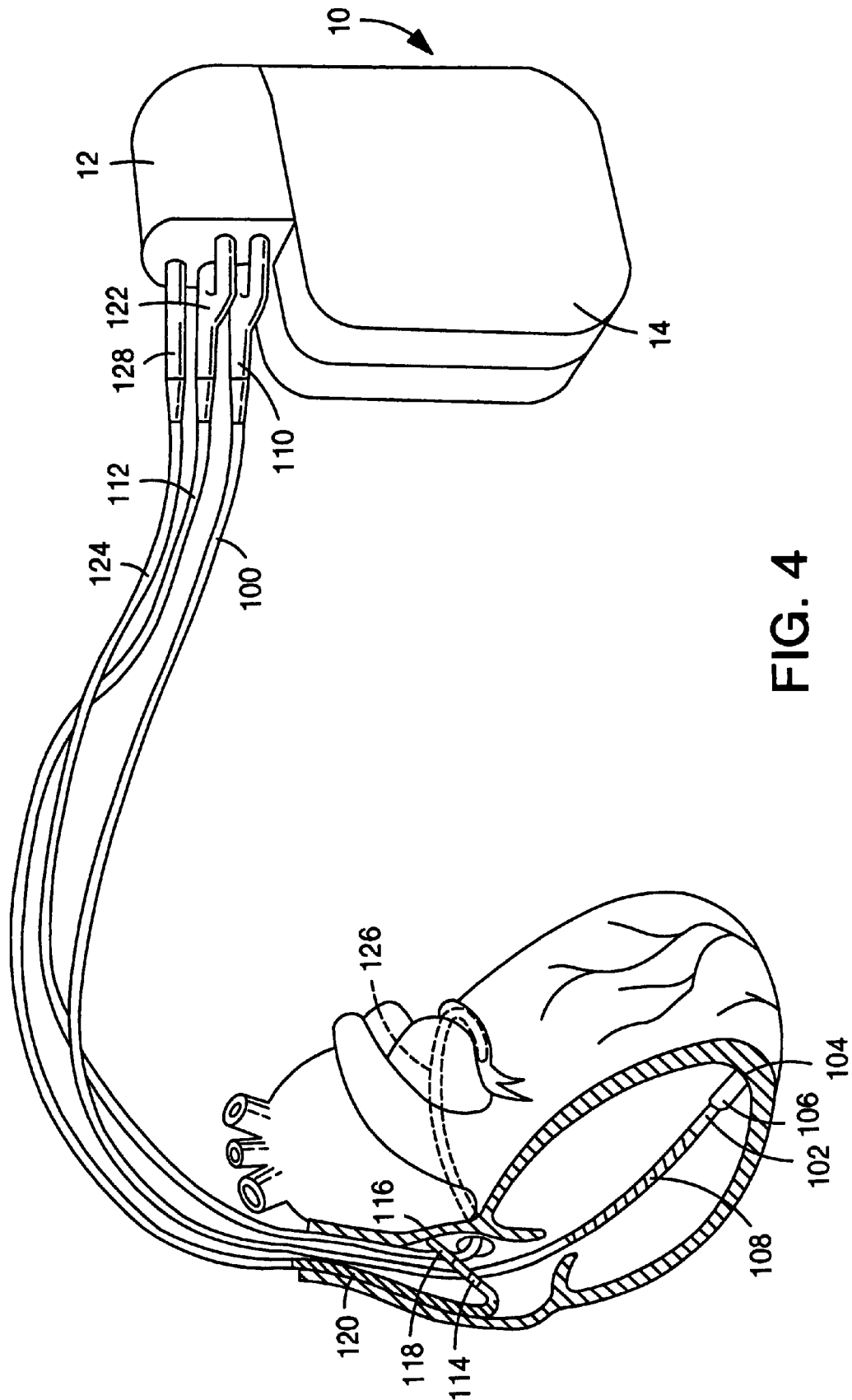
FIG. 4 illustrates one embodiment of an implantable medical device (IMD) and a corresponding lead set used in conjunction with the present invention.
Figure 5:
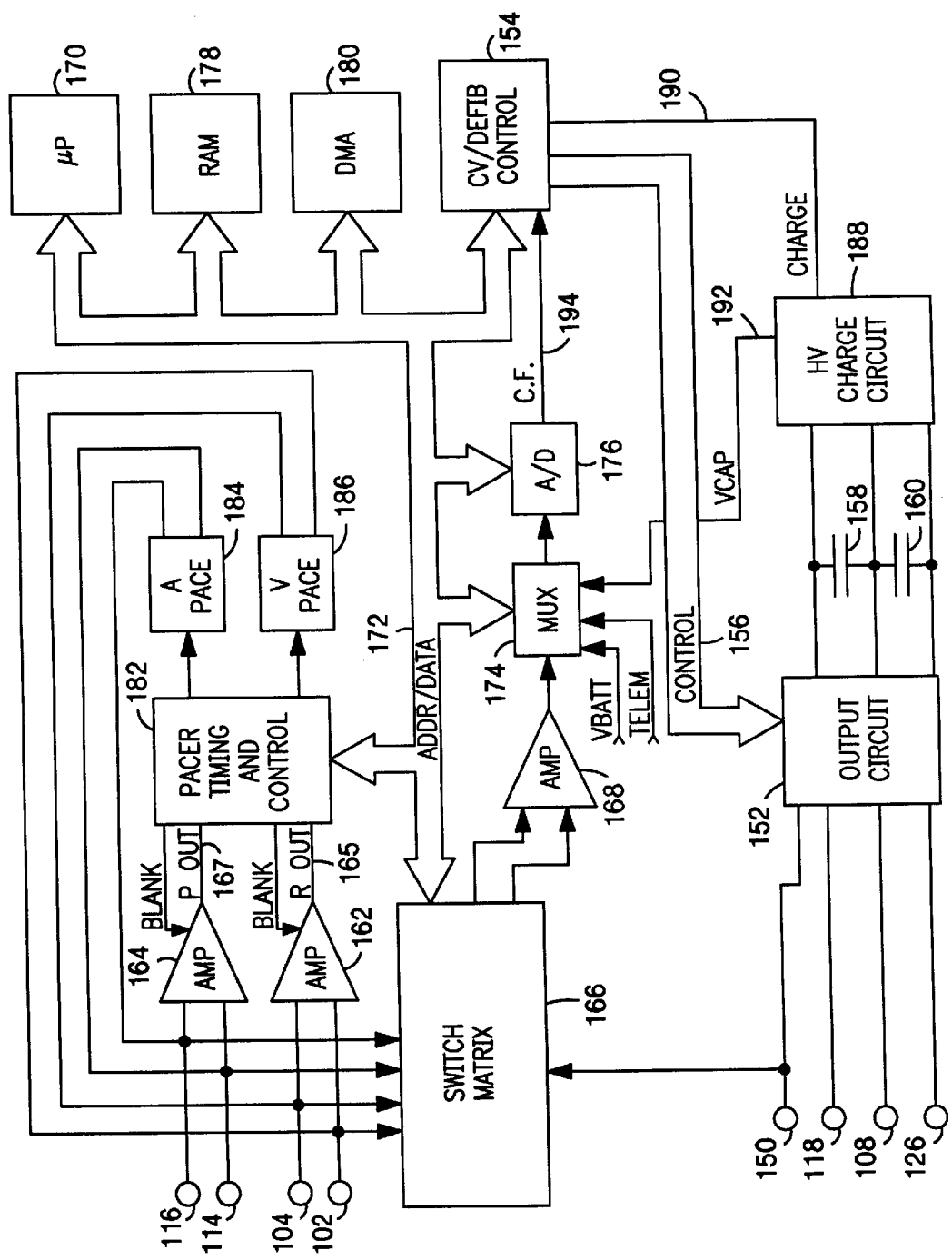
FIG. 5 is a functional schematic diagram of one embodiment of an implantable medical device (IMD) used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 100 carrying three concentric coiled conductors separated from one another by tubular insulative sheaths. Located adjacent the distal end of lead 100 are ring electrode 102, extendable helix electrode 104 mounted retractably within insulative electrode head 106 and elongated coil electrode 108. Each of the electrodes is coupled to one of the coiled conductors within lead body 100. Electrodes 102 and 104 are employed for cardiac pacing and for sensing ventricular depolarizations. At the proximal end of the lead is bifurcated connector 110 which carries three electrical connectors, each coupled to one of the coiled conductors.

Elongated coil electrode 108, which is a defibrillation electrode 108 may be fabricated from platinum, platinum alloy or other materials known to be usable in implantable defibrillation electrodes and may be about 5 cm in length.

The atrial/SVC lead shown in FIG. 4 includes elongated insulative lead body 112 carrying three concentric coiled conductors separated from one another by tubular insulative sheaths corresponding to the structure of the ventricular lead. Located adjacent the J-shaped distal end of the lead are ring electrode 114 and extendable helix electrode 116 mounted retractably within an insulative electrode head 118. Each of the electrodes is coupled to one of the coiled conductors within lead body 112. Electrodes 114 and 116 are employed for atrial pacing and for sensing atrial depolarizations. Elongated coil electrode 120 is provided proximal to electrode 114 and coupled to the third conductor within lead body 112. Electrode 120 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 122 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 124 carrying one coiled conductor coupled to an elongated coiled defibrillation electrode 126. Electrode 126, illustrated in broken outline in FIG. 4, is located within the coronary sinus and great vein of the heart. At the proximal end of the lead is connector plug 128 carrying an electrical connector coupled to the coiled conductor. Elongated coil defibrillation electrode may be about 5 cm in length.

IMD 10 is shown in FIG. 4 in combination with leads 100, 112 and 124, and lead connector assemblies 110, 122, and 128 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 150 in FIG. 5 includes the uninsulated portion of the housing of TIMD 10. Electrodes 150, 118, 108 and 126 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of a capacitor bank (which includes capacitors 158 and 160) during delivery of defibrillation pulses.

Electrodes 102 and 104 are located on or in the ventricle of the patient and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium of the patient and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold. The general operation of R-wave and P-wave amplifiers 162 and 164 may correspond to that disclosed in U.S. Pat. No. 5,117,824 to Keimel et al., hereby incorporated by reference herein in its entirety.

Switch matrix 166 is used to select which of the available electrodes are coupled to wide band (0.5–200 Hz) amplifier 168 for use in digital signal analysis. Selection of electrodes is controlled by microprocessor 170 via data/address bus 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The duration of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 102, 104, 112 and 116. Escape interval counters are also reset on generation of pacing pulses and thereby control the basic timing of cardiac pacing functions, including anti-tachyarrhythmia pacing. The duration of the intervals defined by escape interval timers are determined by microprocessor 170 via data/address bus 172. The value of the count present in the escape interval counters when reset by sensed R-waves and P-waves may be used to measure the duration of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 182 corresponding to the occurrence of sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182 via data bus 53, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988, and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 170 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 170 activates cardioversion/defibrillation control circuitry 154, which initiates charging of high voltage capacitors 158 and 160 via charging circuit 188, under the control of high voltage charging control line 190. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion pulse is controlled by pacer timing/control circuitry 182. Following delivery of the fibrillation or tachycardia therapy microprocessor 170 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output Circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No.

5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
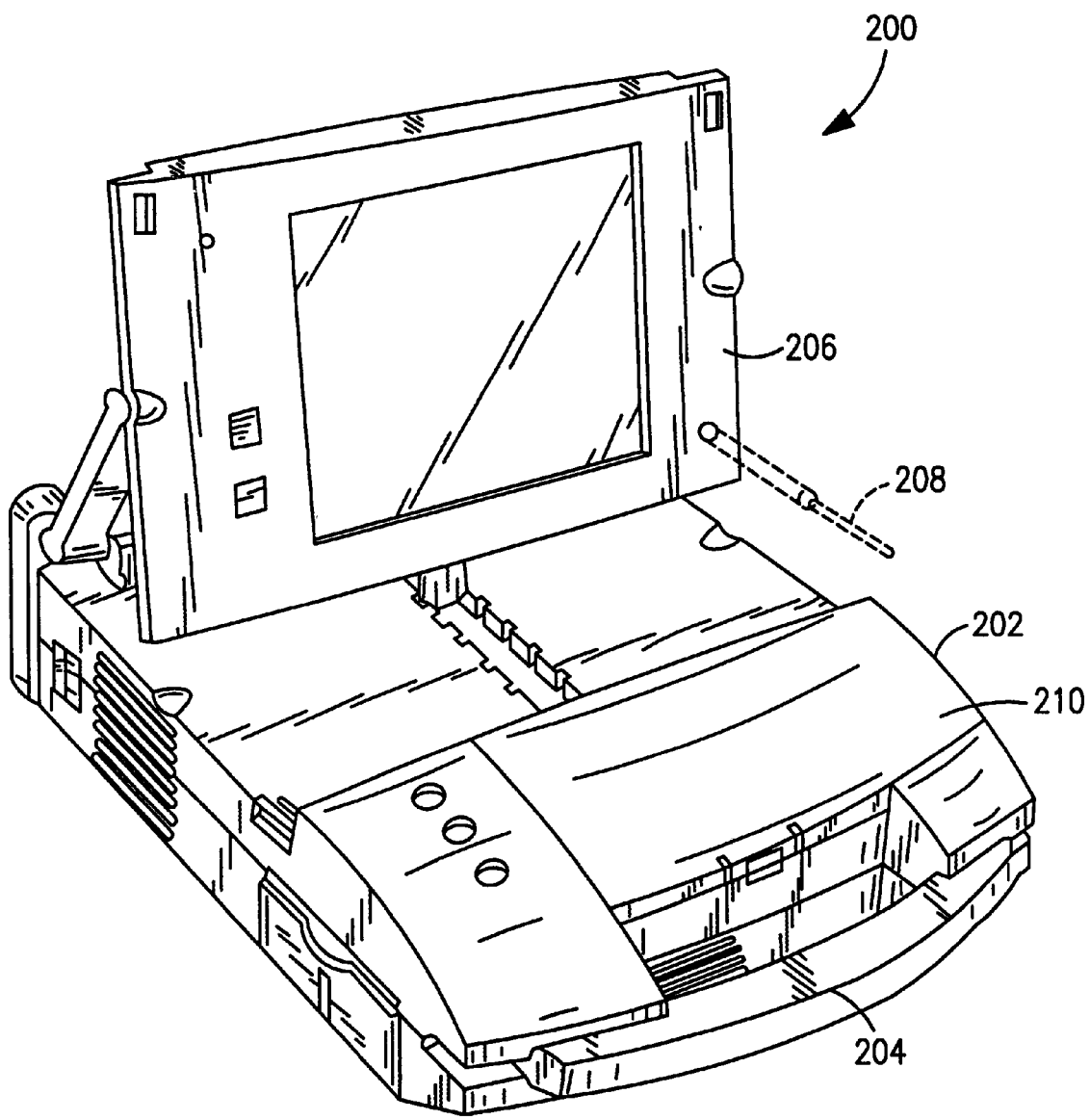
FIG. 6 is a front perspective view of one embodiment of an external programmer apparatus with the display screen opened into one of its viewing positions.

In FIG. 6, a programmer 200 comprises an outer housing 202, which is preferably made of thermal plastics or another suitably rugged yet relatively light-weight material. A carrying handle, designated generally as 204 in the figure, is integrally formed into the front of housing 202. With handle 204, programmer 200 can be carried like a briefcase.

In accordance with one aspect of the present invention, an articulating display screen 206 is disposed on the upper surface of housing 202. Display screen 206 folds down into a closed position when programmer 200 is not in use, thereby reducing the size of programmer 200 and protecting the display surface of display screen 206 during transportation and storage. In the perspective view of FIG. 6, programmer 200 is shown with articulating display screen 206 having been lifted up into one of a plurality of possible open positions such that the display area is visible to a user situated in front of programmer 200. Articulating display screen 206 is preferably of the LCD or electroluminescent type, characterized by being relatively thin as compared to a cathode ray tube (CRT) display, or the like. Display screen 206 is operatively coupled to the computer circuitry disposed within housing 202 and is adapted to provide a visual display of graphics and/or data under control of the internal computer.

In accordance with one aspect of the present invention, display screen 206 is provided with touch-sensitive capability, such that a user can interact with the internal computer by touching the display area of display screen 206 with a stylus 208, or even a user's finger. It is believed that those of ordinary skill in the computer art will be familiar with touch-sensitive display technology, and the details of implementation of such a display will not be described further herein.

Touch sensitive display screen 206 is the primary input medium for programmer 200, and therefore preferably has sufficient resolution to support stylus operations including selection, gestures, annotation, and character recognition. In an alternative embodiment of the present invention, display screen 206 is not touch sensitive, and an alternative selection mechanism (e.g., mouse, trackball, touch pad, or graphics tablet) is used to move a cursor across the screen in order to select and/or activate objects on the screen. In yet another alternative embodiment of the present invention, programmer 200 may contain a voice recognition feature which enables a user to move, select, and activate objects on display screen 206 via voice commands.

A compartment 210 is used for storage of a plurality of patient cables for obtaining a patient's surface ECG. The patient cables convey a patient's surface ECG to internal circuitry of programmer 200, so that the surface ECG can be displayed on display screen 206 or printed out on an internal ECG printer.

Figure 7:
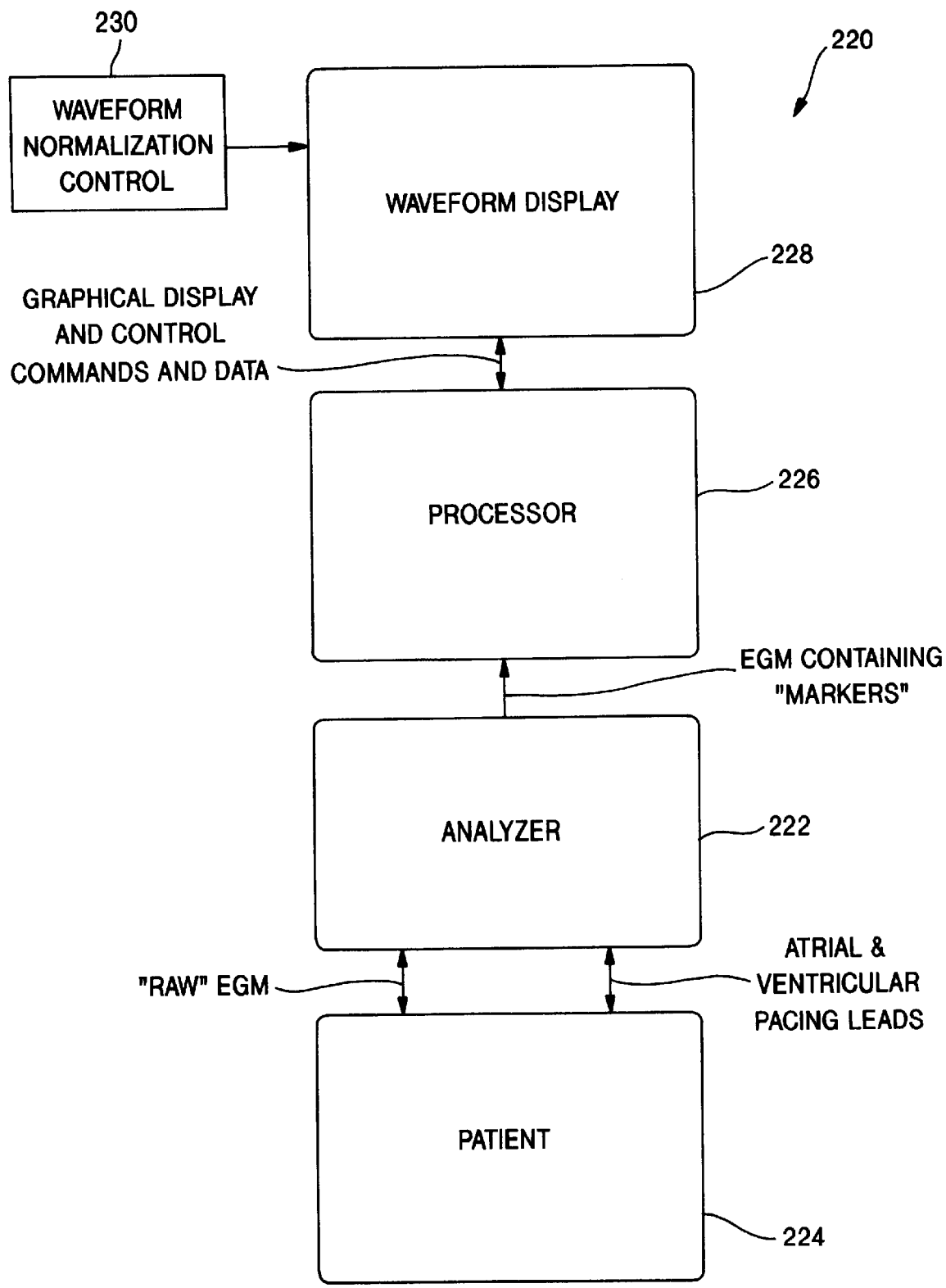
FIG. 7 is a block diagram illustrating the components of an electrogram display system.

FIG. 7 is a block diagram illustrating the components of an electrogram display, shown generally at 220. An analyzer 222 receives a "raw" cardiac signal from the leads connected to a patient's heart 224. Analyzer 222 conditions the raw cardiac signals and inserts markers and digital codes into an electrogram signal that is passed to a processor 226. Markers indicate events such as sensed characteristics of a waveform and also paced events provided to the heart by analyzer 222.

Processor 226 receives the conditioned electrogram from analyzer 222, then processes the electrogram by adding amplitude information. Processor 226 also monitors the content of the electrogram stream for marker information, and if a marker is detected, captures a portion of the electrogram in a display buffer and displays the display buffer data on a waveform display 228. Processor 226 continuously updates the captured portion of the electrogram in the display buffer.

After a waveform is displayed on waveform display 228, a user may normalize the waveform by activating a waveform normalization control 230. After waveform normalization control 230 is activated, a waveform normalization routine is activated within processor 226, which normalizes the waveform signal, such that the waveform signal is resized to a pre-determined nominal height on waveform display 228.

Figure 8:
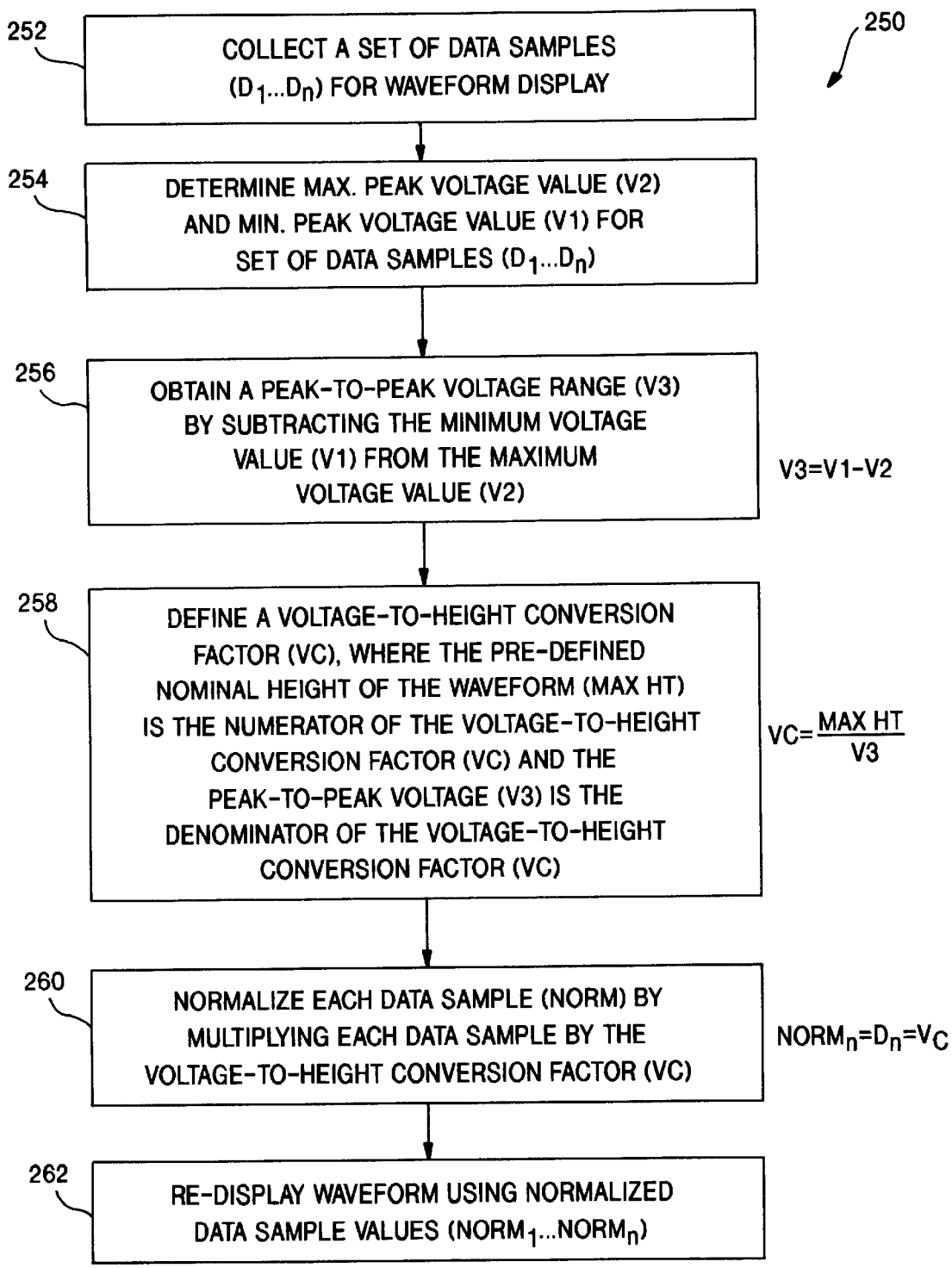
FIG. 8 is a block flow diagram of waveform normalization function in accordance with the present invention.

FIG. 8 is a block flow diagram of waveform normalization function in accordance with the present invention, generally illustrated at 250. The normalization begins by collecting a set of data samples ($D_1 \ldots D_n$), as shown at block 252. Each data sample includes a time component (i.e., the X-axis value) and a voltage component (i.e., the Y-axis value). The collection of data samples are used to construct a waveform display.

After collecting a set of data samples to display, the function next determines the minimum peak voltage value (V1) and the maximum peak voltage value (V2) for the set of data samples ($D_1 \ldots D_n$), as illustrated at block 254. After the minimum and maximum peak voltage values (V1 and V2, respectively) have been determined, the function next obtains a peak-to-peak voltage range value (V3) for the collection of data samples by subtracting the minimum voltage value (V1) from the maximum voltage value (V2) for the set of data samples ($D_1 \ldots D_n$), as illustrated at block 256.

In one embodiment of the present invention, if peak-to-peak voltage range value (V3) is calculated to be very low (e.g., less than 1 mV), peak-to-peak voltage range (V3) may be assigned a larger, hard-coded range value (e.g., approximately 5 mV). This is done so that if there are no EGM signals at startup, the peak-to-peak voltage range will not be normalized to an artificially small range, causing the EGM signals to exceed the bounds of the display when there are actual signals present.

After the peak-to-peak voltage range value (V3) has been determined, the normalize function next establishes a voltage-to-height conversion factor (VC). The pre-defined nominal height of the waveform (MAXHT) provides the numerator of the voltage-to-height conversion factor (VC), and the peak-to-peak voltage range value (V3) provides the denominator for the voltage-to-height conversion factor (VC). A mathematical representation of the voltage-to-height conversion factor (VC) is illustrated below:

$$VC = \frac{MAXHT}{V3}$$

At block 260, the collection of data samples is normalized ($NORM_{1 \ldots n}$) by multiplying the voltage component of each data sample by the voltage-to-height conversion factor (VC) as illustrated by the following equation:

$$NORM_{(1 \ldots n)} = D_{(1 \ldots n)} * VC$$

This normalization ensures that the maximum peak-to-peak voltage range for the collection of data samples is always scaled to a pre-determined nominal height which prevents overlapping of adjacently displayed waveforms. In one embodiment of the present invention, the pre-determined nominal height is defined to be approximately 22 millimeters on the display.

In a preferred embodiment of the present invention, the normalization function is implemented as a computer software application residing and executing within the programmer unit. It is contemplated that the normalization function may also be implemented in firmware, or in a computer hardware circuit design.

Figure 9:
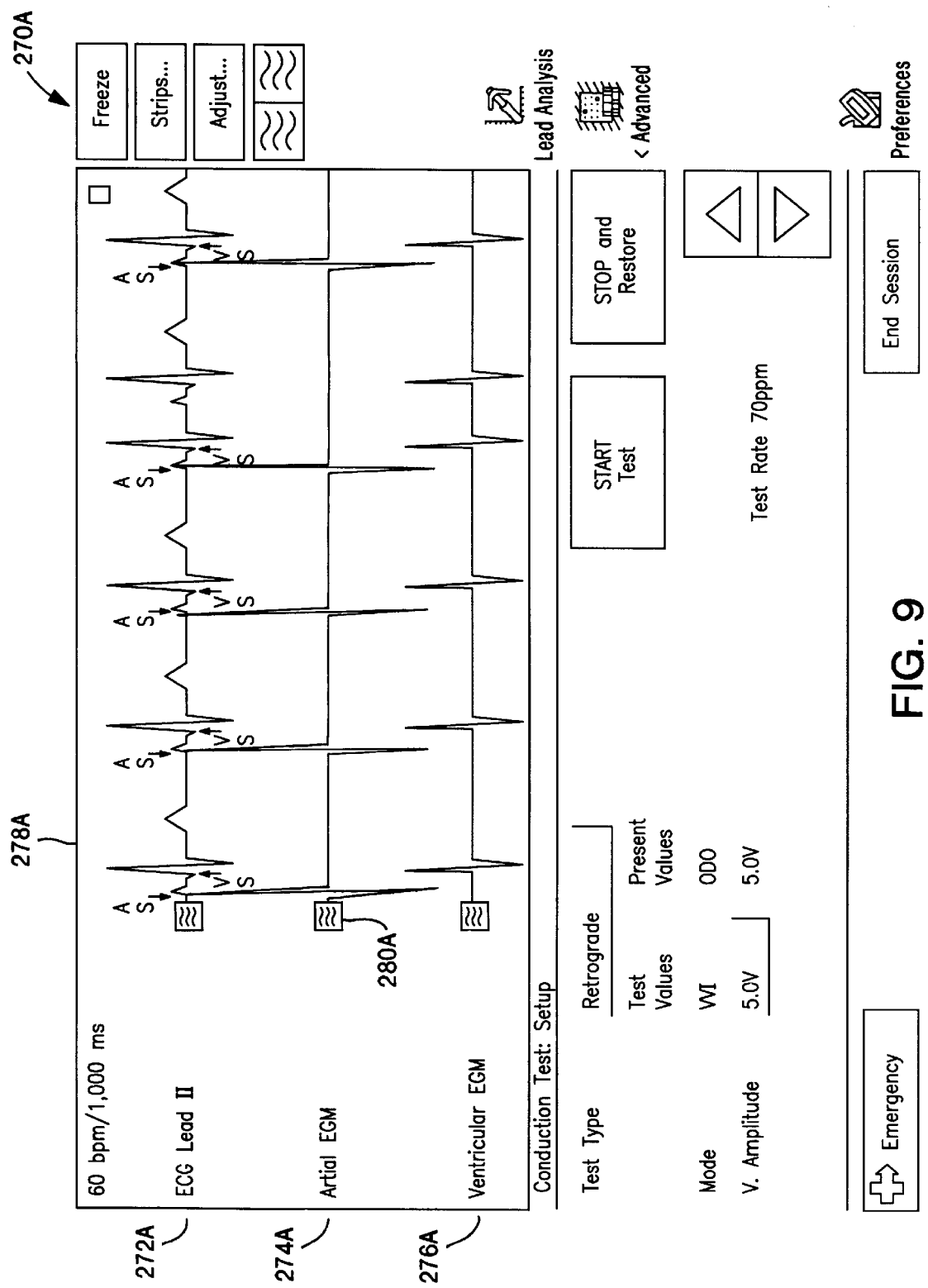
FIG. 9 is an illustration of a programmer display screen, wherein the amplitude of one of the waveforms on the screen encroaches on the display area of adjacent waveforms on the display screen.

FIG. 9 is an illustration of a programmer display screen, wherein the amplitude of one of the waveforms on the screen encroaches the display area of adjacent waveforms on the display screen, as shown generally at 270A. In the waveform display area 278A, three waveforms are displayed: an ECG Lead II waveform 272A, an Atrial EGM waveform 274A, and a Ventricular EGM waveform 276A.

In this illustration, the displayed amplitude of Atrial EGM waveform 274A encroaches on the waveform display of both ECG Lead II waveform 272A and Ventricular EGM waveform 276A. Thus, as a result of the excessive height of Atrial EGM waveform 274A, the display of the adjacent waveforms 272A and 276A is obscured. In this illustrative example, a user wishes to normalize only the Atrial EGM waveform 274A, while leaving the ECG Lead II waveform 272A and Ventricular EGM waveform 276A unchanged.

In order to scale the Atrial EGM waveform 274A to nominal, non-overlapping height, the user selects a "normalize" icon/pushbutton 280A. In the illustrated embodiment, "normalize" icon/pushbutton is located adjacent the leftmost edge of each of the displayed waveforms 272A, 274A, and 276A, and is distinctly identified by a bitmapped pattern of a waveform on the face of icon/pushbutton 280A. Upon selection of the "normalize" icon/pushbutton 280A, the normalize function previously described in FIG. 8 scales the waveform data points such that the peak-to-peak range (i.e., the maximum y-axis data value—the minimum y-axis data value) of the selected waveform does not exceed a pre-determined nominal height.

In one embodiment of the present invention, the analyzer uses an initial default hard coded range of 3 mV for atrial waveforms and 16 mV for ventricular waveforms, prior to normalization.

While the illustrated embodiment provides a preferred method for allowing a user to selectively normalize one or more waveforms on a display screen, the selective normalization of one or more waveforms may be accomplished in a number of alternative ways. In one alternate embodiment, a user may build a set of waveforms to be normalized by selectively pointing to the waveforms to normalize (i.e., "highlighting" the waveforms by selecting them via a pointing device, such as a stylus, mouse, or touchpad), then choosing a single "normalize" button located elsewhere on the screen to complete the normalization process.

In another alternative embodiment, a user may built a selected set of displayed waveforms to nonnalize by entering waveform identifier labels for the desired waveforms at an input device (e.g., a keyboard, or touch sensitive keypad on the display), then activating a "normalize" control on the screen.

In yet another alternative embodiment, a user may selectively identify waveforms to normalize through a voice activated selection process (i.e., voice recognition unit or software present in the programmer/analyzer). For example, the user may issue the voice command, "Normalize ventricular EGM waveform", at which time a voice recognition unit/software within the programmer/analyzer will decode the message, identify the waveforms to normalize, and activate the normalization function on the selected waveforms.

Figure 10:
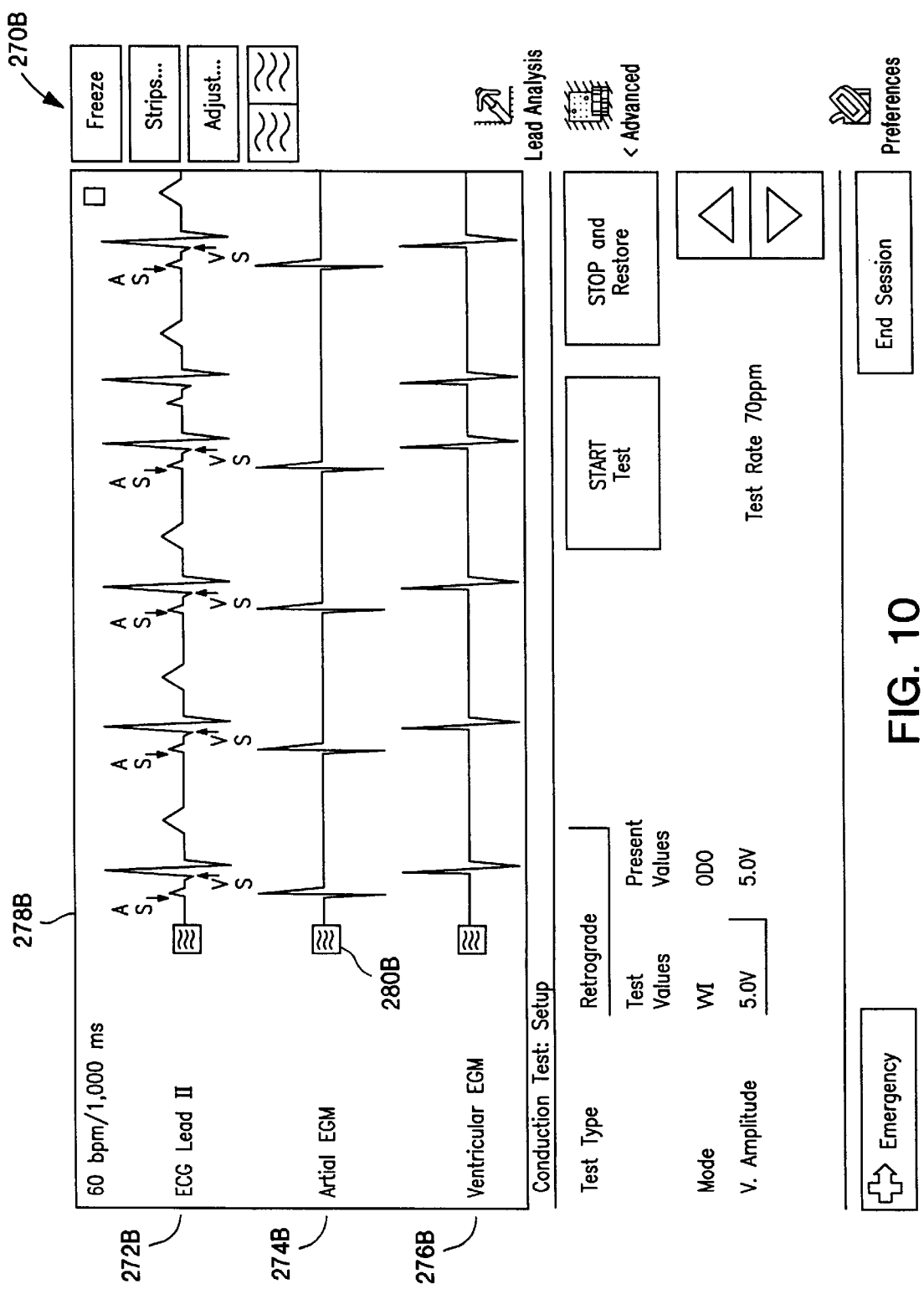
FIG. 10 is an illustration of a programmer display screen, wherein the normalize function has been activated on the encroaching waveform, normalizing the waveform to a pre-determined nominal height.

FIG. 10 is an illustration of a programmer display screen, wherein the normalize function has been activated on the encroaching waveform, normalizing the waveform to a pre-determined nominal height, as shown generally at 270B. In this figure, the display amplitude of Atrial EGM waveform 274B no longer encroaches on the display areas for ECG Lead II waveform 272B and Ventricular EGM waveform 276B. Rather, the display amplitude of Atrial EGM wavefonm 274B is now normalized such that the peak-to-peak range (i.e., the maximum y-axis data value—the minimum y-axis data value) of the displayed waveform does not exceed a pre-determined nominal height.

The waveform normalize feature of the present invention is available in several different display modes of the analyzer. The available display modes include, but are not limited to, a live waveform adjust screen mode, a lead analysis screen mode, a threshold test screen mode, and an advanced test screen mode. As described earlier, the normalization of waveforms is performed on an individual basis. That is, each waveform is independently controlled by its own "normalize" pushbutton.

When the programmer/analyzer is in an emergency mode, the normalize pushbuttons are disabled. After the emergency mode is exited, the normalize pushbuttons are re-enabled.

Figure 11:
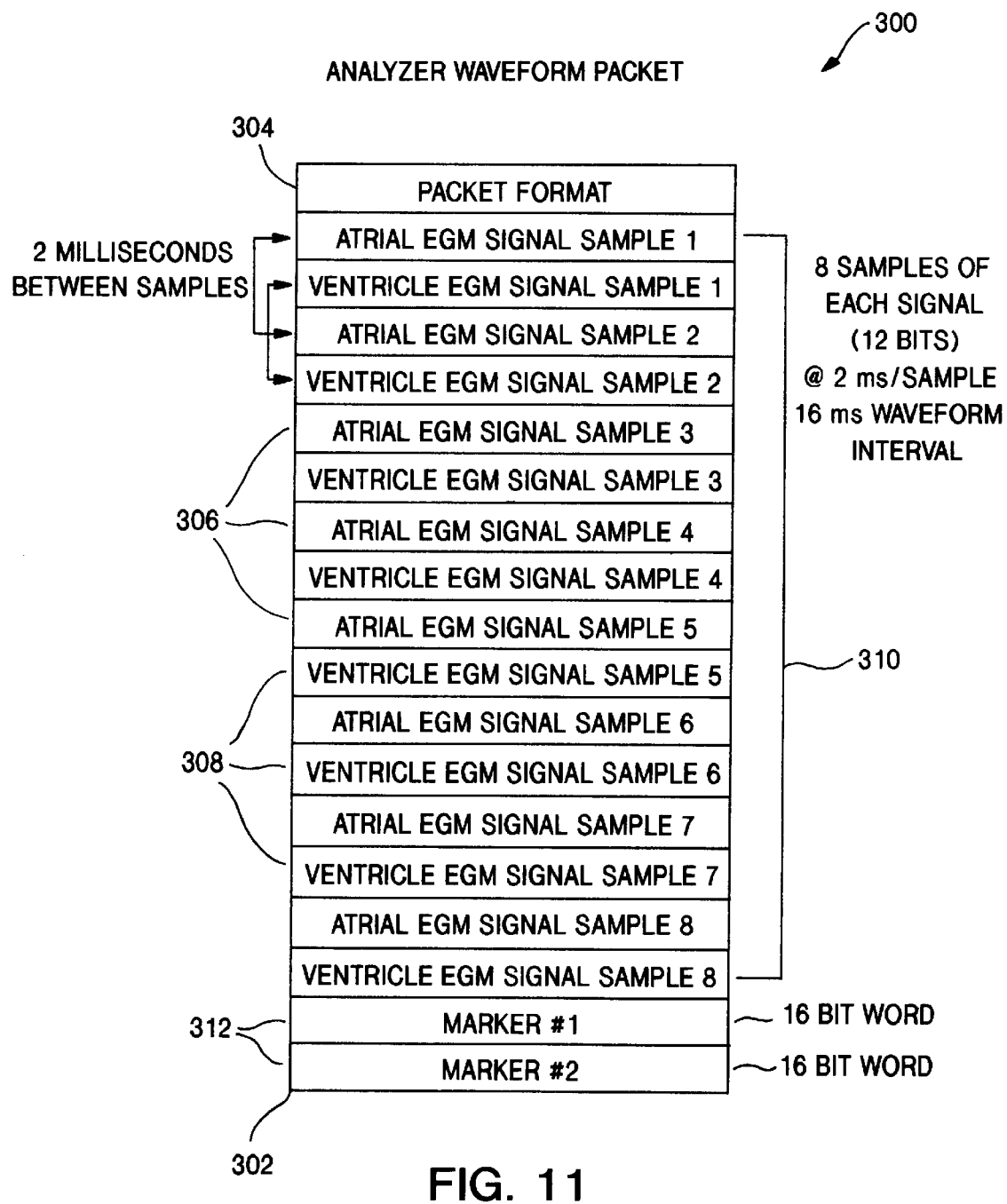
FIG. 11 is a structural diagram of one embodiment of an analyzer waveform packet utilized to package raw EGM signal information for transmission to the programmer/analyzer of the present invention.

FIG. 11 is a structural diagram of one embodiment of an analyzer waveform packet utilized to package raw EGM signal information for transmission to the programmer/analyzer of the present invention, shown generally at 300.

Each time a waveform packet structure 302 is received by the analyzer (i.e., every 16 ms), the data must be decoded from waveform packet structure 302 into separate waveform buffers, one for each signal in the packet. The analyzer will have two EGM signals (typically atrial and ventricle), along with standard markers in its waveform packets. Every 2 milliseconds, a sample is taken from the sorted buffers (one for each signal) and passed to the processor to be processed for the chart recorder, the display, and analog output ports.

The first word of data in waveform packet structure is a format control word 304 which describes the arrangement of the waveform packet. Currently, the analyzer is using only one format, so the field is ignored. It is contemplated that if the analyzer utilizes other packet formats in the future (e.g., different sample widths, different rates, more than two signals, etc.), format control word 304 would be used to index into a configuration table for a descriptor for each possible format.

In the illustrated embodiment, format control word 304 is followed by sixteen EGM signal samples 310. The sixteen EGM signal samples 310 include eight atrial EGM signal samples 306 and eight ventricle EGM signal samples 308, organized in an alternating arrangement. Each EGM signal sample 310 is a twelve bit sample. Each atrial EGM signal sample 306 occurs at a two millisecond interval, and each ventricle EGM signal sample 308 also occurs at a two millisecond interval. Thus, each packet contains a sixteen millisecond waveform interval of both EGM atrial and ventricle signal information.

When a pacing event occurs, a marker 312 will be placed in the data packet following the EGM signal samples 310. Marker 312 consists of sixteen bits which are used by various routines in the analyzer for parsing marker data which follows marker 312.

The highest eight bits of marker 312 contain the marker flag which defines the marker type, while the lower eight bits indexes the marker to one of the EGM signal samples 310. Under this representation, markers can be fixed in time to within two milliseconds instead of sixteen milliseconds. An index of "0" indicates that the marker occurred at the same time as the most recent sample in the current packet. An index of "7" indicates that the current marker occurred at the same time as the earliest sample in the current packet. An index of "8" indicates that the current marker occurred at the same time as the last sample in the previous packet.

Examples of marker types include, but are not limited to: atrial sense, atrial refractory sense, atrial pace, atrial pace with current data, atrial pace with resistance data, ventricular sense, premature ventricular contraction, ventricular refractory sense, ventricular refractory sense (PVC-R), ventricular pace, ventricular pace with current data, ventricular pace with resistance data, and ventricular safety pace. Depending on the type of marker, a variable amount of data will be present for each marker.

In order to unpack analyzer waveform packet 302, EGM signal samples 310 are processed first. The main loop of the analyzer software knows how many total samples (N) and how many different signals (n) there are in analyzer waveform packet 302. In this embodiment, N=16, and n=2. After all EGM waveform samples have been processed by the analyzer, the analyzer examines the length of the packet to determine if markers 312 are present. Thus, if the packet length is more than the expected number of EGM waveform samples 310, there must be markers 312 in the current packet. Not all analyzer waveform packets 302 contain markers 312. In fact, most analyzer waveform packets 302 will not contain markers 312, since markers 312 occur on roughly one-second intervals in the data stream.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electromechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A programmer for graphically displaying information representing an electrogram signal from at least one lead adapted to be positioned within a passageway of a heart and related to an implantable medical device, the programmer comprising:
   an analyzer for receiving the electrogram signal, and transforming the electrogram signal into a plurality of voltage data samples;
   a processor for receiving the voltage data samples from the analyzer;
   a display controlled by the processor to display one or more waveforms representing the plurality of voltage data samples in one or more display modes; and
   an activable waveform normalization control associated with each of the one or more waveforms on the display to a predetermined normal height.

2. The programmer of claim 1, wherein the waveform normalization control is a user activated pushbutton.

3. The programmer of claim 2, wherein the user activated pushbutton is labeled with an identifying icon.

4. The programmer of claim 3, wherein the waveform normalization control is located adjacent each of the one or more waveforms.

5. The programmer of claim 4, wherein the waveform normalization control is located on the left side of each of the one or more waveforms.

6. The programmer of claim 1, wherein the one or more display modes include a live waveform adjust screen.

7. The programmer of claim 1, wherein the one or more display modes include a lead analysis screen.

8. The programmer of claim 1, wherein the one or more display modes include a threshold test screen.

9. The programmer of claim 1, wherein the one or more display modes include an advanced test screen.

10. The programmer of claim 1, wherein said activable waveform normalization control of each of the one or more waveforms is independent of any other normalization operation.

11. The programmer of claim 1, wherein said activable waveform normalization control on each of the one or more waveforms of a waveform display adjusts the height of the one or more waveforms such that the waveforms are non-overlapping.

12. The programmer of claim 11, wherein the pre-determined height of the normalized waveforms is approximately 22 millimeters on the display.

13. The programmer of claim 1, wherein the electrogram signal received by the analyzer includes an EGM signal.

14. The programmer of claim 1, wherein the electrogram signal received by the analyzer includes an electrocardiogram (ECG) signal.

15. The programmer of claim 1, wherein a minimum peak voltage value (V1) and a maximum peak voltage value (V2) are obtained from the plurality of voltage data samples prior to implementation of said activable waveform normalization control, and wherein a peak-to-peak voltage (V3 is obtained by subtracting the minimum voltage value (VD from the maximum voltage value (V2).

16. The programmer of claim 15, wherein a voltage-to-height conversion factor (VC) is defined such that the pre-determined nominal height of the waveform (MAXHT) becomes the numerator of the voltage-to-height conversion factor (VC), and the peak-to-peak voltage (V3) becomes the denominator of the voltage-to-height conversion factor (VC).

17. The programmer of claim 16, wherein the waveform normalization control normalizes the plurality of data samples by multiplying each data sample by the voltage-to-height conversion factor (VC).

18. A system for graphically displaying information related to an implantable medical device, the system comprising:
   at least one electrical lead positioned within a passageway of a heart;
   an analyzer for receiving an electrogram signal from the electrical lead and for transforming the electrogram signal into a plurality of voltage data samples;

a processor for receiving the plurality of voltage data samples from the analyzer;

a display buffer for momentarily capturing a portion of the plurality of voltage data samples;

updating means for continuously updating the captured portion of the plurality of voltage data samples;

a display controlled by the processor for displaying the captured portion of the plurality of voltage data samples as a waveform; and a waveform normalization control associated with the waveform for normalizing the waveform on the display to a pre-determined nominal height.

19. The system of claim 18, wherein the waveform normalization control is a user activated pushbutton.

20. The system of claim 19, wherein the user activated pushbutton is labeled with an identifying icon.

21. The system of claim 20, wherein the waveform normalization control is located adjacent the waveform.

22. The system of claim 21, wherein the waveform normalization control is located on the left side of the waveform.

23. The system of claim 18, wherein the normalization of the waveform is independent of any other normalization operation.

24. The system of claim 18, wherein activation of the waveform normalization control on the waveform adjusts the height of the waveform such that the waveform does not overlap any adjacent waveforms.

25. The system of claim 24, wherein the height of the normalized waveform is approximately 22 millimeters on the display.

26. The system of claim 18, wherein the electrogram signal is an EGM signal.

27. The system of claim 18, wherein the electrogram signal is an ECG signal.

28. The system of claim 18, wherein a minimum peak voltage value (V1) and a maximum peak voltage value (V2) is obtained from the plurality of voltage data samples prior to implementation of said activable waveform normalization control, and wherein a peak-to-peak voltage (V3) is obtained by subtracting the minimum voltage value (VI) from the maximum voltage value (V2).

29. The system of claim 28, wherein a voltage-to-height conversion factor (VC) is defined such that the pre-determined nominal height of the waveform (MAXHT) becomes the numerator of the voltage-to-height conversion factor (VC), and the peak-to-peak voltage (V3) becomes the denominator of the voltage-to-height conversion factor (VC).

30. The system of claim 29, wherein the waveform normalization control normalizes the plurality of data samples by multiplying each data sample by the voltage-to-height conversion factor (VC).

31. An activable waveform normalization apparatus for actively normalizing N displayed waveforms, wherein the N displayed waveforms are displayed vertically aligned atop one another with respect to time, the waveform normalization apparatus comprising:

N waveform normalization controls, wherein each of the N waveform normalization controls corresponds to one of the N displayed waveforms, and wherein activation of one of the N waveform normalization controls normalizes a corresponding displayed waveform to a pre-determined nominal height.

32. The waveform normalization apparatus of claim 31, wherein the normalization controls of one of the N displayed waveforms is independent of any other normalization operation.

33. The programmer of claim 31, wherein the N waveform normalization controls are user activated pushbuttons.

34. The programmer of claim 33, wherein each of the user activated pushbuttons is located adjacent to a corresponding displayed waveform.

35. A method of graphically displaying information representing an electrogram signal from at least one lead positioned in a passageway of a heart and related to an implantable medical device, the method comprising:

receiving the electrogram signal;

transforming the electrogram signal into a plurality of voltage data samples;

displaying N waveforms representing the plurality of voltage data samples;

receiving a user directive to normalize at least one of the N waveforms; and normalizing the at least one of the N waveforms specified in the user directive to a predetermined nominal height.

36. The method of claim 35, wherein the user directive is generated by activating a normalize pushbutton on the display.

37. The method of claim 36, wherein the normalize pushbutton is labeled with an identifying icon.

38. The method of claim 37, wherein the normalize pushbutton corresponds to one of the N waveforms, and is located adjacent the one waveform.

39. The method of claim 35, wherein the user directive is generated by:

selecting at least one of the N waveforms, and activating a normalize pushbutton on the display to normalize the selected waveforms.

40. The method of claim 35, wherein the user directive is generated by a voice activated command.

41. The method of claim 35, wherein the normalization further comprises:

determining the highest voltage sample value within the plurality of voltage data samples and the lowest voltage sample value within the plurality of voltage data samples;

calculating a voltage range by subtracting the lowest voltage sample value from the highest voltage sample value;

defining a voltage-to-height conversion factor wherein the pre-determined nominal height of the waveform becomes the numerator of the voltage-to-height conversion factor, and the voltage range becomes the denominator of the voltage-to-height conversion factor, multiplying each voltage sample by the voltage-to-height conversion factor to receive a normalized voltage sample value; and displaying the normalized voltage sample values on the display.

* * * * *

UNITED STATES PATENT AND TRADEMARK OFFICE
CERTIFICATE OF CORRECTION

PATENT NO.   : 6,266,566 B1  
DATED        : July 24, 2001  
INVENTOR(S)  : Timothy J. Nichols, A. Martin Bradleyk and Robert Werner It is certified that error appears in the above-identified patent and that said Letters Patent is hereby corrected as shown below:

Column 16,  
Line 5, after "waveforms" insert -- for normalizing the one or more waveforms --.  
Line 6, delete "normal" and insert -- nominal --.  
Line 44, after "obtained" insert -- by said processor --.  
Line 47, delete "(VD" and insert -- V1 --.  
Line 63, after "lead" insert -- adapted to be --.

Column 17,  
Line 10, delete "a" and insert -- an activable --.  
Lines 38 and 40, after "obtained" insert -- by said processor --.  
Line 44, after "defined" insert -- by said processor --.

Signed and Sealed this

Eleventh Day of March, 2003

JAMES E. ROGAN  
*Director of the United States Patent and Trademark Office*